(12) United States Patent
Beck et al.

(10) Patent No.: US 7,725,154 B2
(45) Date of Patent: May 25, 2010

(54) METHOD AND MEDICAL IMAGING APPARATUS FOR PLANNING AN IMAGE ACQUISITION BASED ON A PREVIOUSLY-GENERATED REFERENCE IMAGE

(75) Inventors: Walter Beck, Erlangen (DE); Klaus Mayer, Eckental (DE); Cecile Mohr, Erlangen (DE); Jochen Zeltner, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 92 days.

(21) Appl. No.: 11/472,645

(22) Filed: Jun. 22, 2006

(65) Prior Publication Data
US 2006/0293588 A1    Dec. 28, 2006

(30) Foreign Application Priority Data
Jun. 22, 2005    (DE) .................. 10 2005 028 873

(51) Int. Cl.
*A61B 5/05*    (2006.01)
(52) U.S. Cl. .................................... 600/407
(58) Field of Classification Search ............... 600/410, 600/407
See application file for complete search history.

(56) References Cited

U.S. PATENT DOCUMENTS

| | | | |
|---|---|---|---|
| 4,731,725 A * | 3/1988 | Suto et al. ............. | 706/46 |
| 6,149,592 A * | 11/2000 | Yanof et al. ........... | 600/427 |
| 6,411,836 B1 * | 6/2002 | Patel et al. ............ | 600/407 |
| 6,458,081 B1 * | 10/2002 | Matsui et al. .......... | 600/437 |
| 6,506,155 B2 * | 1/2003 | Sluis .................... | 600/437 |
| 6,603,494 B1 * | 8/2003 | Banks et al. .......... | 715/807 |
| 6,614,873 B1 * | 9/2003 | Taylor et al. ......... | 378/62 |
| 6,678,703 B2 * | 1/2004 | Rothschild et al. ... | 707/201 |
| 6,904,161 B1 * | 6/2005 | Becker et al. ........ | 382/128 |
| 7,015,935 B2 | 3/2006 | Herget et al. | |
| 2003/0023155 A1 * | 1/2003 | Tsunoda ............... | 600/407 |
| 2003/0139944 A1 * | 7/2003 | Carlsen et al. ...... | 705/2 |
| 2003/0156745 A1 * | 8/2003 | Saito et al. .......... | 382/128 |
| 2004/0087850 A1 * | 5/2004 | Okerlund et al. ... | 600/407 |
| 2004/0215490 A1 * | 10/2004 | Duchon et al. ...... | 705/2 |
| 2005/0049493 A1 * | 3/2005 | Kerby et al. ........ | 600/437 |

FOREIGN PATENT DOCUMENTS

WO    WO 2005/051197    6/2005

* cited by examiner

*Primary Examiner*—Brian Casler
*Assistant Examiner*—Peter Luong
(74) *Attorney, Agent, or Firm*—Schiff Hardin LLP

(57) ABSTRACT

In a method and device for planning an examination of an examination subject in an imaging diagnosis device, a reference image is selected, and an image of the examination subject is to be made that corresponds to the reference image. A workflow protocol is determined with which the reference image was generated. The acquisition of all required images of the examination subject is planned using this workflow protocol. The workflow protocol is executed for creation of an image of the examination subject that corresponds to the reference image.

8 Claims, 2 Drawing Sheets

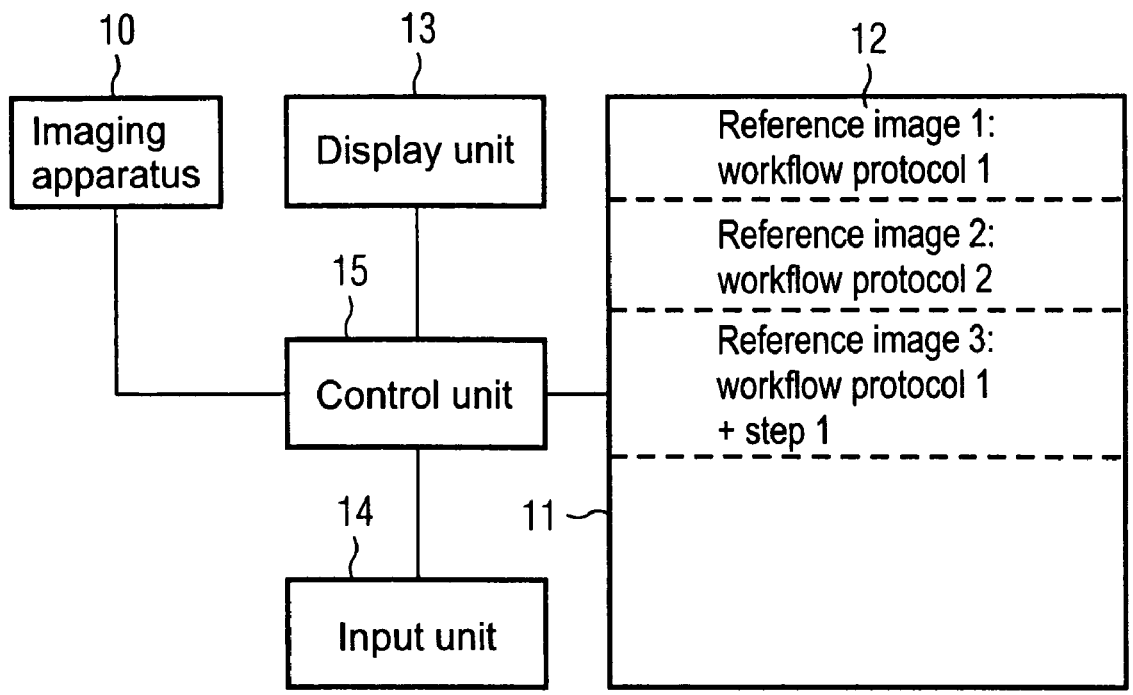
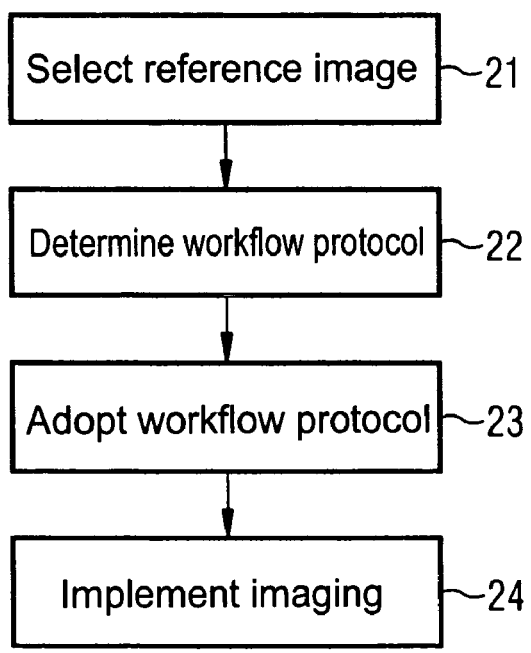

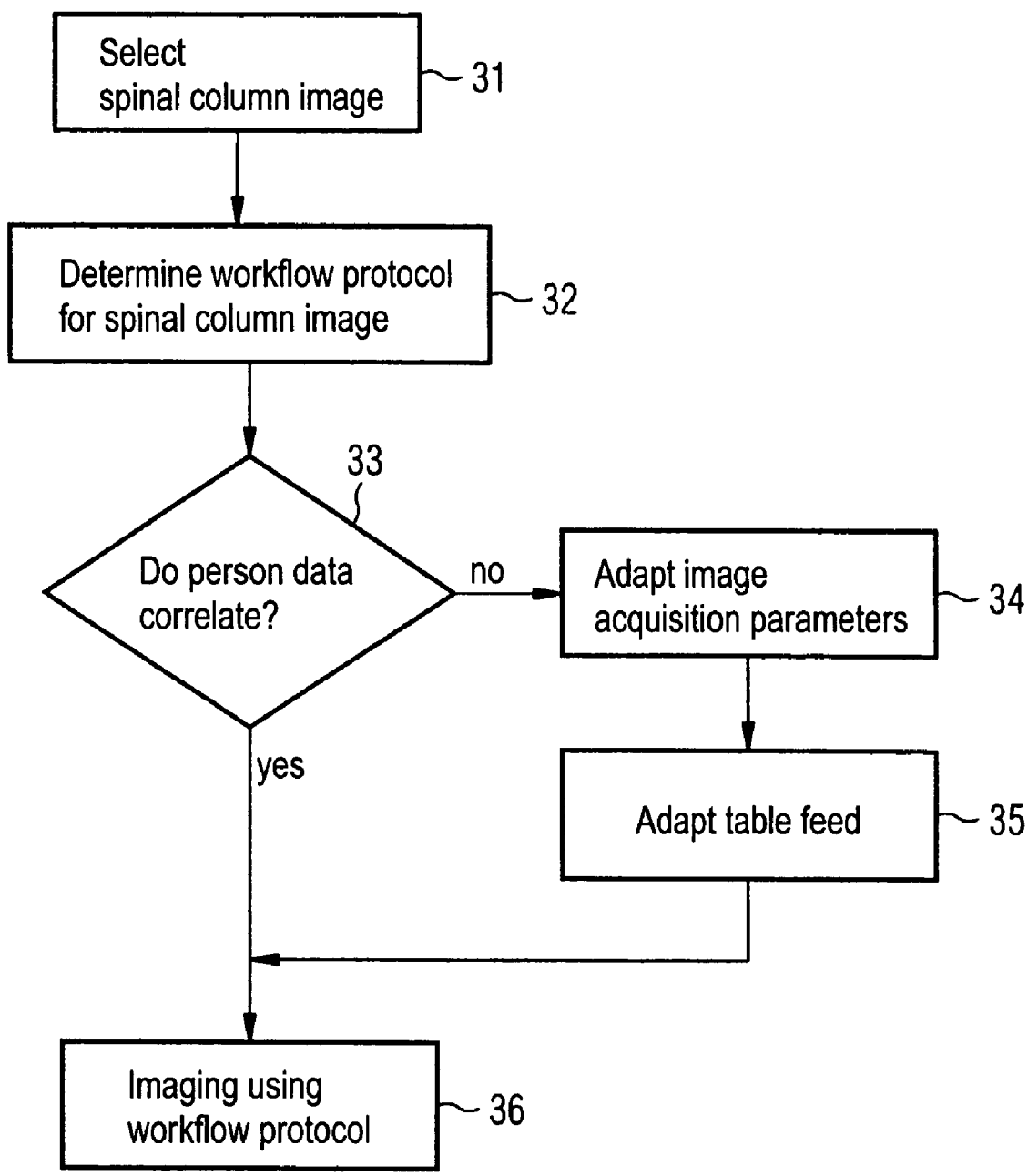

METHOD AND MEDICAL IMAGING APPARATUS FOR PLANNING AN IMAGE ACQUISITION BASED ON A PREVIOUSLY-GENERATED REFERENCE IMAGE

BACKGROUND OF THE INVENTION

1. Field of the Invention

The present invention concerns a method for planning an examination of an examination subject in an imaging diagnosis device as well as an imaging diagnosis device for this purpose. The invention can in particular (but not exclusively) be applied in magnetic resonance systems in which the magnetic resonance images (MR images) that were acquired by the examination subject can be post-processed in different manners.

2. Description of the Prior Art

Magnetic resonance systems are increasingly used in radiology in the examination of patients since they enable a relatively exposure-free examination of the patient as well as the appraisal of different body regions with different contrast performance. Many different post-processing possibilities have been developed in order to be able to process the acquired MR images with various post-processing steps and to be able to better respond to a specific clinical question.

Furthermore, in magnetic resonance tomography techniques have been developed with which the entire body of an examined person can be shown step-by-step as a magnetic resonance image, with the person being moved through the scanner, similar to computed tomography.

For this purpose, exposures of various regions of the body are made at various positions of the patient table and these individual exposures are then combined into a total exposure. Among other things, with these techniques it is possible to represent the entire-spinal column or the entire vascular system of an examination person by combining the individual images with image post-processing methods.

In the prior art, for the planning of an examination it is likewise known to retrieve images of earlier measurements with the respective measurement parameters and to incorporate these images into the planning of a measurement of an examination person, with the same measurement parameters being used as in the sought reference measurement.

If an operating person now wants to repeat a measurement that has led to a reference image for the generation of which a number of images and/or post-processing steps were necessary, the operating person must use the initial images with which the reference images were previously generated by post-processing, which must now be repeated with the present examination subject. The post-processing steps must hereby be created manually, without support by the imaging diagnosis device. This leads to a time-consuming planning of an examination.

SUMMARY OF THE INVENTION

An object of the present invention is to simplify and to accelerate the planning of examinations so that among other things, reference images for the generation of which a number of initial images and/or a number of post-processing steps were necessary, can be used in a simple manner.

This object is achieved by a method for planning an examination of an examination subject with an imaging diagnosis device in accordance with the invention, wherein a reference image is first selected, and an image of the examination subject is to be made that corresponds to that selected reference image. A workflow protocol is determined with which this reference image was generated by the diagnosis device. The acquisition of an image of the examination subject using this workflow protocol, or the acquisition of all required images of the examination subject, is subsequently planned and the workflow protocol is subsequently executed in order to generate an image of the examination subject that corresponds to the reference image. Due to the fact that the workflow protocol that was necessary to generate the reference image can be determined, a reference image can be selected in the planning of an examination of the examination subject and the diagnosis device implements the examination with the workflow protocol that was used with the reference image. Only individual measurements or their parameters could be incorporated into the workflow planning in the prior art, but the possibly-present post-processing procedures of the individual images could not be reconstructed in the prior art. This is possible with the invention by storage of the workflow protocols with the reference images.

In a preferred embodiment, the workflow protocol includes the imaging parameters and the post-processing steps allowing the post-processing procedure of the reference image to be completely reconstructed. For a simple clinical diagnosis it is often required to post-process an image acquired by the diagnosis device, be it via application of filter functions or be it via formation of subtraction of various images in order, for example, to make the intensity curve better visible given use of a contrast agent. If the selected reference image was composed of a number of "raw" reference output images, the post-processing steps that were necessary in order to arrive at the reference image can now be reconstructed. The planning can now be simplified via the access to the reference image with the corresponding workflow protocol since the possibly-necessary post-processing steps no longer have to be executed manually, but instead are automatically employed as well upon selection of the reference image.

The post-processing protocols are stored together with the reference images, or at least include a "linking" between accessed reference image and the post-processing protocol, such that the post-processing protocol is also available upon selection of the reference image.

The workflow protocol preferably includes the imaging parameters that are necessary for generation of a reference output image as well as the post-processing steps in order to generate the reference image from the reference output image. As mentioned above, images are often acquired and subsequently post-processed for a better diagnosis. According to this embodiment of the invention, the workflow protocol includes the parameters of the reference output image as well as the image processing steps with which the final reference image was generated from the reference output image. If an arbitrary image from a complex examination is selected as a reference image for the new examination, the entire examination workflow that had led to the reference image can be reconstructed and applied in the new measurement. It is also possible that, given selection of an arbitrary image from a complete examination as a reference image for a new examination, the complete workflow up to this result is reconstructed, so that only parts of an examination need to be newly started.

Furthermore, the reference image can be an image of the examination subject that comprises at least two individual images, whereby the reference image was generated via post-processing of the at least two individual images. If the combined reference image is selected for the planning of a new measurement, the individual images no longer have to be selected as in the prior art and the post-processing no longer has to be effected manually. Instead, by selection of the reference image the workflow protocol that had led to the reference image is automatically used in the planning of the new measurement, with the imaging parameters of the individual images and the post-processing steps that were necessary in order to generate the total reference image from the individual images being taken into account.

Furthermore, according to another embodiment of the invention it is possible to record the patient-specific data of the examination protocol. These patient-specific data in the examination protocol can then be compared with the person-specific data of the patient to be examined, and the examination protocol can subsequently be adapted to the current examined person. If the sought reference image is, for example, a combined image in which the complete spinal column is shown, this could have been implemented (for example) by three individual measurements with three different table positions, with the three individual images being subsequently combined into an overall image. The patient bed or the table on which the examination subject is located, however, must be displaced between the individual measurements so that the respective examined region always lies within the magnet of the magnetic resonance system. This table feed now depends on the size of the patient. Given the adoption of the workflow protocol, the parameters that depend on the patient are now adapted to the current patient. For example, the planned table displacement between the measurements turns out to be larger in the event that the current patient is greater than that on which the reference measurement was implemented for generation of the reference image. If the varying size of the patient were not taken into account, this could lead to gaps or superfluous overlapping upon assembly of the individual images into an overall image.

Furthermore, the at least two individual images from which the reference image was generated can be images in which the examination subject was positioned differently in the diagnosis device (advantageously the magnetic resonance system).

The invention likewise concerns an imaging diagnosis device for generation of an image of an examination person with an imaging device for generation of the image of the examination person and a storage unit for storage of reference images and for storage of workflow protocols with whose help the reference images were generated, with the reference images being stored in connection with their workflow protocols.

Furthermore, an input unit is provided in order to select a reference image as well as a control unit that determines the workflow protocol that has led to the generation of the reference image and which, using the selected workflow protocol of the reference image, controls the workflow of the examination of the examination person such that the imaging apparatus acquires an image of the examination person that corresponds to the reference image.

DESCRIPTION OF THE DRAWINGS

FIG. 1 schematically illustrates an imaging diagnosis device according to the invention.

FIG. 2 is a flowchart with which an examination can be planned by selection of a reference image in accordance with the invention.

FIG. 3 is a flowchart for planning a spinal column image of an examination subject in accordance with the invention.

DESCRIPTION OF THE PREFERRED EMBODIMENTS

An imaging diagnosis device (here a magnetic resonance system) is schematically shown in FIG. 1. The functioning of a magnetic resonance system for generation of slice images of the body by nuclear magnetic resonance is known to those skilled in the art and need not be described in detail herein. For clarity, only the components that are necessary for understanding of the present invention are shown.

The magnetic resonance system has an imaging apparatus (scanner) that, as is known in the prior art, acquires MR images of the examination subject. In the planning of a new examination, the operating person of the magnetic resonance system can access reference images stored in a storage unit 11, when images of the current examination person are to be generated that correspond to the reference image with the respective image acquisition parameters. Data sets 12 are stored in the storage unit 11. A data set 12 includes a reference image and the associated workflow protocol that has led to the generation of the reference image. The workflow protocol typically includes the imaging parameters such as echo time, repetition time, field of view, matrix size etc. Furthermore, the workflow protocol includes all possible post-processing steps with which the post-processing procedure of the reference image can be reconstructed. For example, if the reference image 1 is an image that comprises a number of individual "raw" reference images, the workflow protocol thus includes the measurement parameters of the individual reference output images and the post-processing steps that are necessary in order to generate the reference image 1 from the individual reference output images.

Not all of the previously involved protocol steps need be specified for each reference image with a number of post-processing steps. In such cases, as indicated with reference image 3 in FIG. 1, it is possible to refer to another workflow protocol or another reference image and to store possible additional steps in the event that they are present.

The workflow protocols do not have to be physically stored together with the reference images; they can also be stored separately, but a connection between the reference image and workflow protocol that is inclusive of the post-processing steps must exist so that the post-processing steps that have led to the selected reference image are also available upon selection of a reference image.

If the operating person now wants to plan a new examination, he or she can select a reference image from the storage unit 11 via a display unit 13 and selection via an input unit 14. A control unit 15 now determines the workflow protocol that has led to the selected reference image. The control unit 15 subsequently controls the imaging apparatus 10 in the manner that implements an examination of the examination person using the selected workflow protocol, so that an image of the examination person is acquired that corresponds to the reference image. As is explained in detail in connection with FIG. 3, the parameters that depend on the examination person data (such as, for example, the field of view or the table displacement, which can be dependent on the body size of the examined patient) can be compared and adapted with the current patient data given adoption of the workflow protocols in the planning.

Shown in FIG. 2 are the method steps with which the planning of a measurement can be simplified and made faster. For example, in a first step 21 the operating person of the magnetic resonance system selects a reference image that should serve as a basis for a measurement. For the patient situated in the magnetic resonance system, an image that corresponds to the reference image is to be acquired. If the reference image is now known, in a step 22 the workflow protocol is determined that led to the reference image. In a step 23, the workflow protocol that was determined in step 22 and that belonged to the reference image selected in step 21 is finally adopted and applied to the current examined person. In step 23, the imaging can then be implemented with the adopted workflow protocol, which leads to an image that corresponds to the reference image that was applied in step 21.

A further embodiment of the invention is shown in FIG. 3, wherein the planning of a spinal column acquisition with the aid of magnetic resonance tomography is explained in detail. As shown in step 31, the operating person can, for example, select an MR image as a reference image that shows the entire spinal column. In a step 32, the workflow protocol that led to the spinal column image can then subsequently be determined via access to the storage unit 11. In the present example, the workflow protocol could, for example, exhibit the following steps: measurement of the head with predetermined image acquisition parameters; table displacement a1; measurement of the abdomen with predetermined image acquisition parameters; table displacement a2; measurement of the legs. The reference image that shows the entire spinal column of the examination person is then generated from the three individual images.

Before the determined workflow protocol is incorporated into the planning of the measurement for a current patient, the workflow protocol can be adapted to the registered examination person. For this reason, in step 33 it is checked whether the person data of the reference image correlate with the current person data. If this is not the case, the image acquisition parameters can be adapted to the current person parameters in a step 34. This can be, for example, adaptation of the field of view. Furthermore, the table feed between the individual measurements can have an incorrect value for the person to be examined in the case of the measurements of the spinal column. In the event that the current examined person is larger than that on whom the reference measurement was implemented, the planned table displacement turns out to be greater; if the current examined person is smaller, the planned table displacement turns out to be smaller (step 35).

Finally, in step 36 the imaging can then be implemented using the workflow protocol. In the case of the spinal column measurement, for example, the measurement of the head with the image acquisition parameters of the workflow protocol determined in step 32 can first be used again; a table displacement b1 adapted to the current patient subsequently follows; followed by the measurement of the abdomen, with geometric parameters being adapted to the body size of the current examination person. The table displacement b2, adapted in turn to the body size of the current examined person, and then the concluding measurement of the legs subsequently ensue with the measurement parameters of the reference measurement, with the geometric parameters were possibly being adapted to the body size.

If the person data of the reference image coincide with the current person data, the workflow protocol can be entirely adopted. After the imaging in step 36, an overall image of the spinal column of the current examined patient is then automatically created.

The present invention has a number of advantages: examinations with a number of examination steps can be planned using a single reference image, with the entire workflow and possibly-implemented post-processing steps that have led to the reference image being taken into account. This means that all different measurements whose images were necessary for generation of the reference image are automatically available again for the planning. Furthermore, the measurement parameters that depend on the examined person are automatically adapted to the current examined person. A significant time savings hereby results in the preparation of a measurement and a simplification of the workflow. It is likewise possible to exchange data of complete examinations such that they are usable for other examination subjects. The invention is not limited to the application in magnetic resonance systems. The invention can be used in every imaging diagnosis device in which a number of workflow steps with possible post-processing steps are necessary for generation of images. The workflow protocol need not be stored together with the reference image as shown in FIG. 1. Other storage formats are possible, and it must be ensured only that the associated workflow protocol can be reconstructed given selection of a reference image.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical imaging apparatus comprising:
    a scanner configured to interact with an examination subject to acquire raw image data therefrom using raw image data acquisition parameters;
    a storage unit containing a plurality of reference images previously acquired with said scanner using respective workflow protocols, each of said reference images and the workflow protocol therefor being linked in said storage unit, and said workflow protocol including said raw image data acquisition parameters and post-processing steps for implementing a post-processing procedure applied to an image reconstructed from said raw image data to generate said reference image;
    a control unit that operates said scanner;
    an input unit that accesses said storage unit to allow manual selection of only a reference image corresponding to a current image of an examination subject to be generated through said control unit to cause the selected reference image to be supplied to said control unit together with the workflow protocol linked thereto without separate manual selection of said workflow protocol; and
    said control unit being supplied, as a result of said manual selection of only reference image, with said workflow protocol linked to said reference image, and being configured to operate said scanner to acquire current raw imaging data for said current image using said raw image data acquisition parameters in said workflow protocol linked to said reference image obtained from said storage unit, and said control unit being configured to generate said current image from at least one reconstructed image that is reconstructed from the acquired current raw imaging data by applying, to said reconstructed image, the post-processing steps in the workflow linked to said reference image, to generate said current image.

2. A method for planning acquisition of image data from an examination subject in a medical imaging apparatus, comprising the steps of:
    storing a reference image in a memory and in said memory linking said reference image, with a workflow protocol with which the reference image was generated, said workflow protocol including raw image data acquisition parameters to acquire raw image data in a scanner, and post-processing steps that implement a post-processing procedure on a reconstructed image that is reconstructed from said raw image data to generate said reference image;

for generating a current image of a subject in said scanner corresponding to said reference image, manually selecting only said reference image from said memory and causing the manual selecting of only said reference image to automatically retrieve the reference image together with the workflow protocol linked thereto in said memory, without separate selection of said workflow protocol;

automatically electronically planning acquisition of current raw image data for said current image with said scanner using said raw image data acquisition parameters in the workflow protocol linked to said reference image to generate a planned protocol;

executing the planned protocol to acquire current raw image data for said current image with said scanner; and automatically reconstructing a reconstructed image from the current raw image data acquired for the current image, and applying, to said reconstructed image, said post-processing steps in said workflow protocol linked to said reference image, to generate said current image.

3. A method as claimed in claim 2 comprising storing a plurality of different reference images in said memory, respectively linked to different workflow protocols, and selecting one of said different reference images, corresponding to said current image, for generating said current image.

4. A method as claimed in claim 2 wherein said medical imaging apparatus is a magnetic resonance imaging apparatus, and wherein the step of executing said workflow protocol for generating said current image comprises executing a workflow protocol for acquiring magnetic resonance image data from said subject for generating said current image.

5. A method as claimed in claim 2 wherein said reference image is comprised of a plurality of individual images and comprising, in said workflow protocol generation of said individual images and post-processing thereof to form said reference image, and wherein said workflow protocol for generating said current image comprises acquiring data for a plurality of individual images and combining said individual images to form said current image.

6. A method as claimed in claim 2 wherein said examination subject is a patient, and comprising the additional steps of:

in said workflow protocol for generating said reference image, including recording of patient-specific data of a patient from whom said reference image was obtained;

comparing the patient-specific data of the patient from whom the current image is to be obtained with the patient-specific data associated with the reference image to obtain a comparison result; and adapting the workflow protocol for generating said current image dependent on said comparison result.

7. A method as claimed in claim 6 wherein said workflow protocol for said reference image comprises acquiring a plurality of individual images at respectively different positions of the patient and combining the individual images to form said reference image, and wherein the step of adapting said workflow protocol for generating said current image comprises adapting respective positions for said patient dependent on said patient-specific data and acquiring data for respective images of said patient at said different positions and combining said respective images to form said current image.

8. A method as claimed in claim 7 comprising placing said patient in said medical imaging apparatus on a displaceable table, and comprising, in said workflow protocol for generating said current image, designating respective table positions for said respective images that form said current image.

* * * * *